(12) United States Patent
Miura et al.

(10) Patent No.: US 11,045,770 B2
(45) Date of Patent: Jun. 29, 2021

(54) SILICA MEMBRANE FILTER

(71) Applicant: NGK INSULATORS, LTD., Nagoya (JP)

(72) Inventors: Aya Miura, Nagoya (JP); Masahiro Furukawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 505 days.

(21) Appl. No.: 15/701,716

(22) Filed: Sep. 12, 2017

(65) Prior Publication Data

US 2018/0001273 A1 Jan. 4, 2018

Related U.S. Application Data

(63) Continuation of application No. PCT/JP2016/058108, filed on Mar. 15, 2016.

(30) Foreign Application Priority Data

Mar. 19, 2015 (JP) .............................. JP2015-055918

(51) Int. Cl.
*B01D 69/12* (2006.01)
*B01D 69/02* (2006.01)
(Continued)

(52) U.S. Cl.
CPC ........... *B01D 69/12* (2013.01); *B01D 61/145* (2013.01); *B01D 63/066* (2013.01);
(Continued)

(58) Field of Classification Search
None
See application file for complete search history.

(56) References Cited

U.S. PATENT DOCUMENTS

| | | | |
|---|---|---|---|
| 5,110,470 A | 5/1992 | Yokosawa et al. | |
| 2008/0093291 A1 | 4/2008 | Isomura et al. | |

(Continued)

FOREIGN PATENT DOCUMENTS

| | | |
|---|---|---|
| CN | 101528328 A | 9/2009 |
| EP | 2 832 428 A | 2/2015 |

(Continued)

OTHER PUBLICATIONS

English translation of International Preliminary Report on Patentability (Chapter I) (Application No. PCT/JP2016/058108) dated Sep. 28, 2017, 8 pages.

(Continued)

*Primary Examiner* — Krishnan S Menon
(74) *Attorney, Agent, or Firm* — Burr & Brown, PLLC (57) ABSTRACT

A silica membrane filter 10 includes an ultrafiltration membrane 15, which is disposed on a support body 14 and which contains an element 14 as a primary component, and a silica membrane 18 which is disposed on the ultrafiltration membrane 15 and which has an aryl group. The ultrafiltration membrane 15 has a structure infiltrated by Si of the silica membrane 18, the atomic ratio A (=Si/M) of Si to the element M in a membrane-side region 16, which is a region corresponding to 25% of the ultrafiltration membrane 15 from the silica membrane 18, satisfies 0.01≤A≤0.5, and the ratio A/B of the atomic ratio A to the atomic ratio B (=Si/M)

(Continued)

in a base-material-side region 17, which is a region corresponding to 25% from the support body 14, is within the range of 1.1 or more.

9 Claims, 4 Drawing Sheets

(51) Int. Cl.
| | |
|---|---|
| *B01D 69/10* | (2006.01) |
| *C01B 33/148* | (2006.01) |
| *B01D 63/06* | (2006.01) |
| *B01D 61/14* | (2006.01) |
| *B01D 67/00* | (2006.01) |
| *B01D 71/02* | (2006.01) |
| *C01B 33/145* | (2006.01) |
| *C07C 7/144* | (2006.01) |
| *C07C 29/76* | (2006.01) |

(52) U.S. Cl.
CPC ......... *B01D 67/0048* (2013.01); *B01D 69/02* (2013.01); *B01D 69/10* (2013.01); *B01D 71/022* (2013.01); *B01D 71/027* (2013.01); *C01B 33/145* (2013.01); *C01B 33/148* (2013.01); *C07C 7/144* (2013.01); *C07C 29/76* (2013.01); *B01D 2325/02* (2013.01); *B01D 2325/04* (2013.01)

(56) References Cited

U.S. PATENT DOCUMENTS

| | | |
|---|---|---|
| 2010/0300960 A1 | 12/2010 | Hishiki et al. |
| 2015/0053605 A1 | 2/2015 | Kawai et al. |

FOREIGN PATENT DOCUMENTS

| | | |
|---|---|---|
| JP | 01-304006 A1 | 12/1989 |
| JP | 03-143535 A1 | 6/1991 |
| JP | 2001-212401 A1 | 8/2001 |
| JP | 2009-255035 A1 | 11/2009 |
| JP | 2010-506698 A1 | 3/2010 |
| JP | 2013-128886 A1 | 7/2013 |
| JP | 2013-226541 A1 | 11/2013 |
| WO | 2008/050813 A1 | 5/2008 |
| WO | 2013/146622 A1 | 10/2013 |

OTHER PUBLICATIONS

International Search Report and Written Opinion (Application No. PCT/JP2016/058108) dated Jun. 7, 2016.
Toshinori Tsuru, et al., "Permporometry Characterization of Microporous Ceramic Membranes," *Journal of Membrane Science*, 186 (2001), pp. 257-265.
Chinese Office Action (with English translation), Chinese Application No. 201680015427.6, dated Nov. 27, 2019 (17 pages).
German Office Action, German Application No. 11 2016 001 283.7, dated Apr. 9, 2021 (6 pages).

SILICA MEMBRANE FILTER

BACKGROUND OF THE INVENTION

1. Field of the Invention

The present invention relates to a silica membrane filter. In particular, the present invention relates to a silica membrane filter that selectively separates an alcohol from an organic fluid mixture.

2. Description of the Related Art

To date, regarding the silica membrane filter, for example, a silica membrane filler produced by coating a porous base material with a precursor sol of silicon alkoxide having a p-tolyl group and by performing drying and firing is proposed (tor example, refer to PTL 1). In such a filter, the ratio of the total mass of silica membrane to the total mass of dried membrane is 38 to 85 percent by mass, and alcohol can be selectively separated from a hydrocarbon and alcohol mixture.

CITATION LIST

Patent Literature

PTL 1: International Publication No. 2013/146622

SUMMARY OF THE INVENTION

According to the silica membrane filter described in PTL 1, a method for manufacturing a silica membrane is further optimized and the silica membrane itself is further optimized. However, the permeation resistance of the entire silica membrane filter has not been sufficiently investigated. As a result, there is a problem in that the permeation resistance of the entire silica membrane filter increases and the permeation rate of a liquid decreases.

The present invention addresses such problems, and a main object of the invention is to provide a silica membrane filter capable of further increasing the permeation rate during separation of an alcohol from an organic fluid mixture.

In order to achieve the above-described object, the present inventors performed intensive research and found that, in the case where the water permeate flow rate of an ultrafiltration membrane serving as an underlying layer was further optimized, the underlying layer was smoothly infiltrated by a material (silica sol or the like) for forming the silica membrane, and the permeation resistance of the target for separation, was able to be reduced. As a result, the present invention was realized.

A silica membrane filter according to the present invent ion comprises an ultrafiltration membrane which is disposed on a support body and which contains an element M as a primary component; and a silica membrane which is disposed on the ultrafiltration membrane and which has an aryl group, wherein the ultrafiltration membrane has a structure infiltrated by Si of the silica membrane, the atomic ratio A (=Si/M) of Si to the element M in a membrane-side region, which is a region corresponding to 25% of the ultrafiltration membrane from the silica membrane, satisfies 0.01≤A≤0.5, and the ratio A/B of the atomic ratio A to the atomic ratio B (=Si/M) in a base-material-side region, which is a region corresponding to 25% of the ultrafiltration membrane from the support body, is within the range of 1.1 or more.

The silica, membrane filter according to the present invention can further increase the permeation rate during separation of ah alcohol from an organic fluid mixture. The reason for this is conjectured as described below, for example. In general, in the case where a silica membrane is formed on a base material, e.g., ceramic, if the water permeate flow rate of an ultrafiltration membrane serving as an underlying layer of the silica membrane is large, the underlying layer is infiltrated by a silica sol that is a raw material for the silica membrane, and the underlying layer is filled with the silica membrane raw material to an extent such that a dense silica membrane is formed on the surface. In this state, if a silica membrane is formed by firing, a silica membrane having the smallest permeation pore diameter is formed up to the underlying layer, the permeation resistance of the entire silica membrane filter may increase, and the permeation rate of a liquid may decrease. Alternatively, even, in the case where the concentration of the sol for forming the silica membrane is increased so as to suppress infiltration of the silica membrane raw material, the amount of silica sol that adheres at a time increases, and cracking of the membrane may occur during firing. Regarding the silica membrane filter according to the present invention, the pore diameter, the membrane thickness, and the like of the ultrafiltration membrane serving as an underlying layer are adjusted, the water permeate flow rate of the ultrafiltration membrane is optimized and, thereby, the structure is made to be optimal for infiltration by the silica sol. therefore, according to the present invention, the permeation resistance is low, and the permeation rate during separation of the alcohol from the organic fluid mixture can be increased.

DETAILED DESCRIPTION OF THE INVENTION

Figure 1:
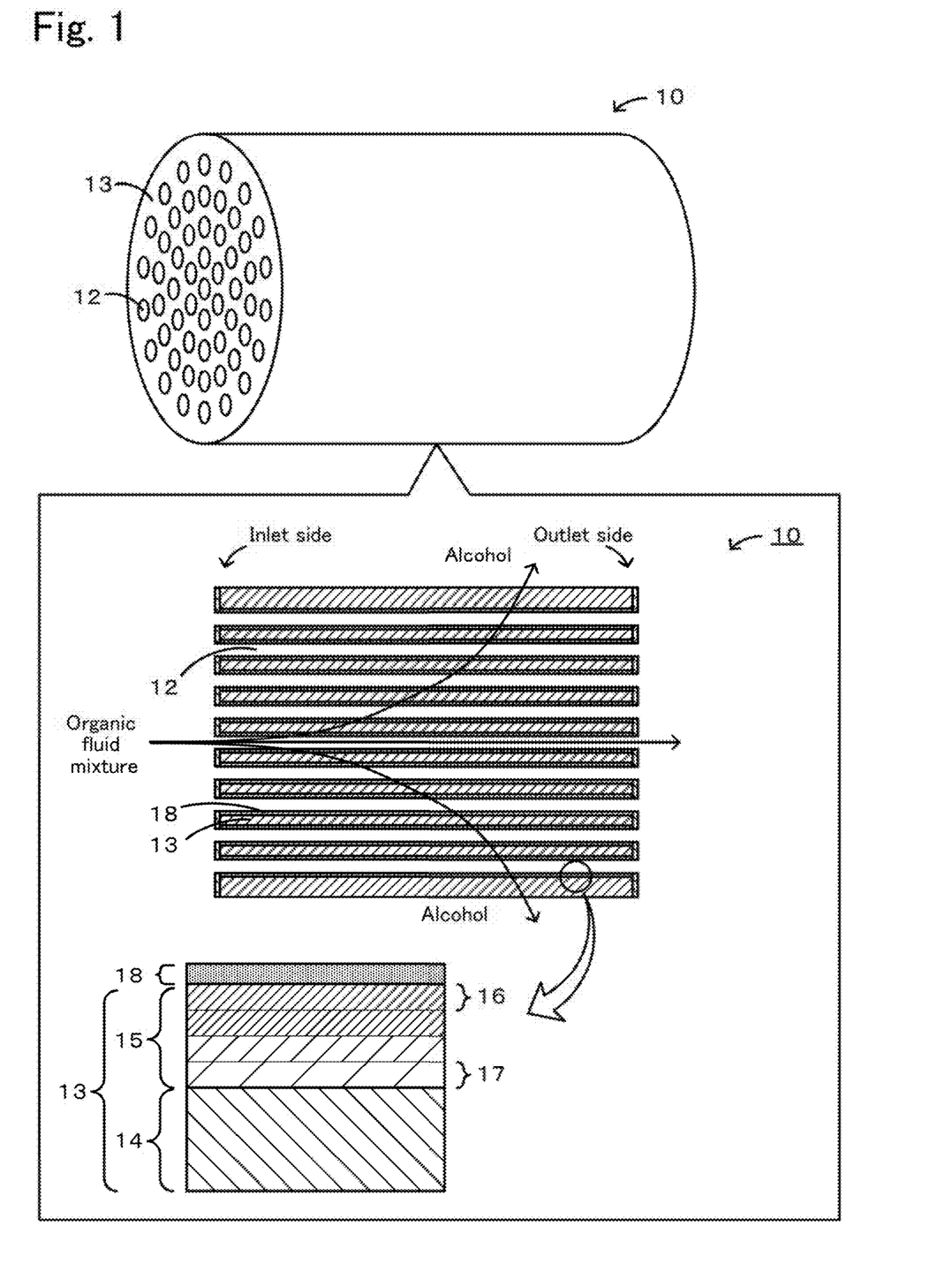
FIG. 1 is an explanatory diagram schematically showing the configuration of a silica membrane filter 10.

Next, the embodiments according to the present invention will be described with reference to the drawings. FIG. 1 is an explanatory diagram schematically showing the configuration of a silica membrane filter 10 according to an embodiment of the present invention. The silica membrane filter 10 according to the present invention includes an ultrafiltration membrane 15 disposed on a support body 14 and a silica membrane 18 disposed on the ultrafiltration membrane 15. The ultrafiltration membrane 15 contains an element M as a primary component and has a structure infiltrated by Si of the silica membrane 18. In addition, the silica membrane 18 has an aryl group. A porous base material 13 includes the support body 14 and the ultrafiltration membrane 15.

An organic fluid mixture is a target for separation and may be, for example, a fluid mixture of a hydrocarbon and an alcohol. Examples of hydrocarbons include xylene and n-octane, and a gasoline component may be included. Examples of alcohols include methanol, ethanol, propanol, and butanol. In particular, the alcohol may be ethanol. The fluid may be a gets or a liquid.

The porous base material 13 is provided with a plurality of cells 12 serving as flow passages of a fluid that is the target for separation. Regarding the silica membrane filter 10, in a fluid, which is a target for the treatment and which enters the cells 12 from the inlet side, an alcohol having a molecular size suitable for permeation through the silica membrane 18 permeates the silica membrane 18 and the porous base material 13 and exits through the side surface of the silica membrane filter 10. On the other hand, a fluid (mainly the hydrocarbon) that cannot permeate the silica membrane 18 flows through the cells 12 serving as the flow passages and exits from the outlet side of the cells 12. The porous base material 13 may have a monolithic structure provided with the plurality of cells 12 or may have a tubular structure provided with a cell. There is no particular limitation regarding the external shape thereof, and the shape can be a circular columnar shape, an elliptical columnar shape, a quadrangular prism shape, a hexagonal prism shape, or the like. Alternatively, the porous base material 13 may have a shape of a tube having a polygonal cross section.

The porous base material 13 may include, for example, the support body 14 and the ultrafiltration membrane 15 disposed on the surface of the support body 14, as shown in FIG. 1. The support body 14 may have a pore diameter of about 0.1 μm to several hundreds of micrometers. Also, the porosity of the support body 14 may be within the range of 20 percent by volume or more and 70 percent by volume or less. Examples of materials constituting the support body 14 may include at least one type of ceramic of alumina (α-alumina, γ-alumina, anodized alumina, and the like), titania, silica, cordierite, zirconia, mullite, and zirconia. Consequently, the porous base material 13 may have excellent heat resistance, chemical resistance, impact resistance, and the like. In particular, alumina is preferable from the viewpoint of production and availability of the base material. It is preferable that the support body 14 be produced by molding and sintering alumina particles serving as the raw material and helving an average particle diameter of 0.001 to 30 μm. The porous base material 13 may have a single-layer structure or a multilayer structure. The support body 14 may include, for example, a fine particle portion provided with the ultrafiltration membrane 15 on the surface and a coarse particle portion provided with the fine particle portion on the surface. The support body 14 may be a member having a pore diameter larger than the pore diameter of the ultrafiltration membrane 15 or may be a member having a porosity higher than the porosity of the ultrafiltration membrane 15. The support body 14 may be a member produced by, for example, extrusion molding or the like or a member provided with a microfiltration membrane of alumina, titania, or the like on the surface.

The ultrafiltration, membrane 15 (also referred to as UF membrane) is a membrane that functions as an underlying layer of the silica membrane 18. For example, the membrane thickness of the ultrafiltration membrane 15 is preferably 0.3 μm or more and more preferably 0.5 μm or more. Meanwhile, the membrane thickness of the ultrafiltration membrane 15 is preferably 5 μm or less, more preferably 3 μm or less, and further preferably 2 μm or less. In the case where the membrane thickness is 0.3 μm or more, the support body 14 can be more reliably covered with the ultrafiltration membrane 15, and infiltration by the Si component can be further suppressed. Meanwhile, in the case where the membrane thickness is 5 μm or less, cracking and the like of the membrane can be suppressed and a denser silica membrane 18 can be formed. The average pore diameter of the ultrafiltration membrane 15 is preferably within the range of 2 nm or more and 20 nm or less. In this range, the silica membrane 18 is easily formed on the surface. The average pore diameter of the ultrafiltration membrane 15 is measured in conformity with the method described in Non-Patent Literature 1 (Journal of Membrane Science 186 (2001) 257-265). In this regard, in the present invention, n-hexane is used as a condensable gas and nitrogen is used as a noncondensable gas.

The ultrafiltration membrane 15 contains an element M. Examples of the element M include Ti, Al, Si, and Zr, and specific examples include at least one type, of ceramic of alumina (α-alumina, γ-alumina, anodized alumina, and the like), titania, silica, cordierite, zirconia, mullite, and zirconia. Consequently, the ultrafiltration membrane 15 may have excellent heat resistance, chemical resistance, impact resistance, and the like. In particular, titania is preferable from the viewpoint of production and availability of the underlying layer.

Figure 2:
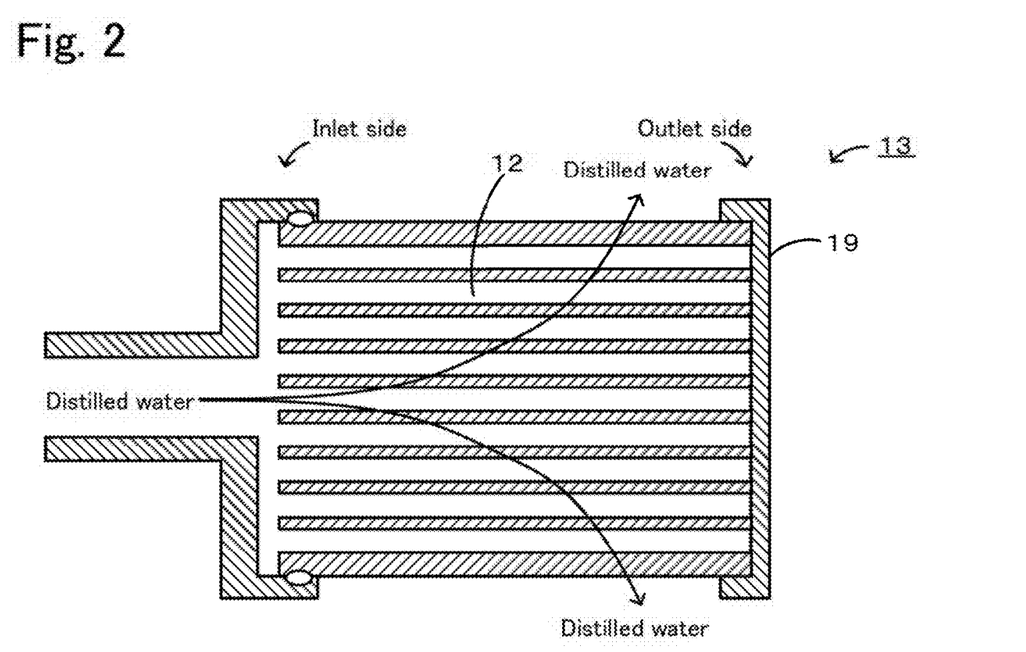
FIG. 2 is an explanatory diagram of a method for measuring the water permeate flow rate.

It is preferable that the water permeate flow rate of the ultrafiltration membrane 15 before provision of the silica membrane 18 be within the range of 0.5 m/day or more and 6.0 m/day or less. In the case where the water permeate flow rate is in this range, for example, the state of infiltration of the ultrafiltration membrane 15 by the raw material component of the silica membrane 18 can be improved. The water permeate flow rate is more preferably 1.0 m/day or more and further preferably 1.2 m/day or more. Meanwhile, the water permeate flow rate is more preferably 5.0 m/day or less and further preferably 4.5 m/day or less. A method for measuring the water permeate flow rate will be described. FIG. 2 is an explanatory diagram of a method for measuring the water permeate flow rate. Regarding the measurement of the water permeate flow rate, initially, a seal portion 19 is disposed on the outlet side of the porous base material 13 including the ultrafiltration membrane 15 (a filter before the silica membrane 18 is formed) so as to create a state in which one end of each of the cells 12 is sealed, as shown in FIG. 2. Then, distilled water is supplied to the cells 12 from the inlet side, and the flow rate, the pressure, and the water temperature of the supplied water are measured. The measured values are converted to values under the condition of pressurization of 0.1 MPa at 25° C., and the amount of water ($m^3$) that passes a unit area of the membrane (permeates the membrane) is assumed to be the water permeate flow rate ($m^3/m^2/day$=m/day).

The ultrafiltration membrane 15 may be produced by using a raw material sol containing the element M. The ultrafiltration membrane 15 may be produced through an ultrafiltration membrane production process including formation treatment for producing a formed body by forming the raw material sol on the surface of the support body 14, drying treatment for drying the formed body, firing treatment for firing the dried formed body, and the like. Here, the formation treatment, the drying treatment, and the firing treatment may be repeated a plurality of times. The raw material sol has to contain the element M and is, for example, titania sol. In addition, additives, e.g., a binder and a thickener, may be added to the raw material sol. Examples of the additives include polyvinyl alcohol (PVA). In the formation treatment, the raw material sol may be poured into the cells 12 of the porous base material 13. The drying treatment has to remove a solvent included in the raw material sol and can be performed in air at roost temperature to 120° C., for example. The firing treatment can be performed at a temperature at which the raw material sol, as an oxide, adheres to the support foody 14, and the temperature can be set to be, for example, 350° C. to 800° C. In the ultrafiltration membrane production process, the amount of the membrane that adheres (membrane thickness) may be appropriately adjusted by the raw material sol concentration, the number of times of film formation, and the like and the pore diameter may be appropriately adjusted by the firing temperature and the amount of the additives added such that the above-described membrane thickness and the like are achieved.

The silica membrane 18 is disposed on the ultrafiltration membrane 15 and is a membrane selectively permeable to an alcohol in the organic fluid mixture. Here, "selectively permeable to an alcohol" includes not only separation and removal of an alcohol having a purity of 100% from the organic fluid mixture, but also separation and removal of a solution or gas having a high alcohol content compared with the composition of the organic fluid mixture. For example, an alcohol having a purity of 90% or more or an alcohol having a purity of 95% or more may be separated and removed. The membrane thickness of the silica membrane 18 may be within the range of, for example, 30 nm or more and 200 nm or less. In the case where the membrane thickness is 30 nm or more, the strength of the membrane can be further enhanced, and in the case of 200 nm or less, the permeation rate of the alcohol that is a target for separation can be ensured. The membrane thickness of the silica membrane 18 is preferably 50 nm or more and preferably 100 nm or less. The silica membrane 18 may be provided with pores having a size of 0.5 nm or more and 20 nm or less. Permeation of alcohol can be facilitated in such a pore range. The pore diameter of the silica membrane 18 can be measured by a method based on the Kelvin equation, for example, by using a pore distribution measuring apparatus (DYNAMIC PORE SIZE MEASUREMENT) produced by SRI International. In the measurement, nitrogen gas can be used as feed gas and n-hexane can be used as condensable gas.

The silica membrane 18 has an aryl group. Examples of the aryl group include a phenyl group, a benzyl group, a tolyl group, and a xylyl group. From the viewpoint of the alcohol permeability, a tolyl group and a phenyl group are preferable, and a p-tolyl group is particularly preferable. In this regard, the silica membrane 18 may be produced from a raw material in which an aryl group directly bonds to Si.

The silica membrane 18 may be produced by using a raw material sol containing Si. Examples of the raw material sol containing Si include a precursor sol of silicon alkoxide having an aryl group. In particular, it is preferable that an aryl group directly bond to Si in the raw material sol. The silica membrane 18 may be produced through a membrane production process including, for example, membrane formation treatment for producing a membrane formed body by forming a membrane of the raw material sol on the surface of the ultrafiltration membrane 15, drying treatment for drying the membrane formed body, firing treatment for firing the dried formed body, and the like. Here, the membrane formation treatment, the drying treatment, and the firing treatment may be repeated a plurality of times. In the membrane formation treatment, the raw material sol may be poured into the cells 12 of the porous base material 13. The drying treatment has to remove a solvent included in the raw material sol and can be performed in air at room temperature to 120° C., for example. The firing treatment can be performed at a temperature at which the raw material sol, as an oxide, adheres to the ultrafiltration membrane 15, and the temperature can be set to be, for example, 350° C. to 550° C.

In the case where a cross section of the silica membrane filter 10 is observed by an electron microscope and the thickness of the entire ultrafiltration membrane 15 is assumed to be 100%, a region corresponding to 25% of the ultrafiltration membrane 15 from the silica membrane 18 is represented as a membrane-side region 16, and a region corresponding to 25% of the ultrafiltration membrane 15 from the support body 14 is represented as a base-material-side region 17. Here, the atomic ratio A (=Si/M) of Si to the element M in the membrane-side region 16 of the ultrafiltration membrane 15 satisfies $0.01 \leq A \leq 0.5$. In addition, the ratio A/B of the atomic ratio A to the atomic ratio B (=Si/M) in the base-material-side region of the ultrafiltration membrane 15 is within the range of 1.1 or more. That is, in the ultrafiltration membrane 15, the concentration of Si infiltrated is relatively low in the membrane-side region 16 and, in addition, the concentration in the base-material-side region 17 tends to be lower than the concentration in the membrane-side region 16. In the case where such a range is satisfied, the permeation rate during separation of the alcohol from the organic fluid mixture can be more increased. The ratio A/B of the atomic ratio A to the atomic ratio B (=Si/M) in the base-material-side region 17 of the ultrafiltration membrane 15 is further preferably within the range of 1.2 or more. In this regard, it is preferable that. A/B further increase. However, in the case where, for example, 100<A/B holds, the silica membrane filter 10 has a structure in which the ultrafiltration membrane is hardly infiltrated by Si and adhesiveness between the silica membrane 18 and the ultrafiltration membrane 15 is degraded, which is not preferable. Alternatively, it is not preferable because cracking of the membrane may occur in such a case due to difference in the thermal expansion between the silica membrane 18 and the ultrafiltration membrane 15 during firing. More preferably, the atomic ratio A of the ultrafiltration membrane 15 satisfies $0.1 \leq A \leq 0.5$. In this range, the permeation rate during separation of the alcohol from the organic fluid mixture can be more increased. Meanwhile, it is more preferable that the atomic ratio B of the ultrafiltration membrane 15 satisfy $0.01 \leq B \leq 0.4$.

Figure 3:
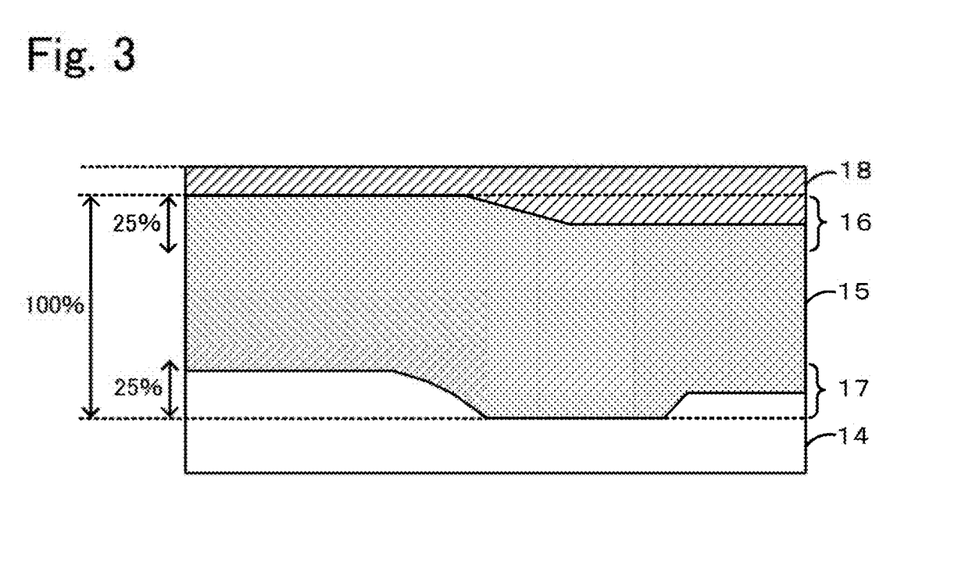
FIG. 3 is an explanatory diagram of the thickness of the ultrafiltration membrane 15.

Here, the method for determining the thickness of the ultrafiltration membrane 15 and the method for calculating the atomic ratios A and B will be described. FIG. 3 is an explanatory diagram of the thickness of the ultrafiltration membrane 15. Initially, the silica membrane filter 10 is cut such that cross sections of the support body 14, the ultrafiltration membrane 15, and the silica membrane 18 can be observed. Subsequently, the cross sections are observed by an electron microscope. Observation by the electron microscope is performed at the magnification at which the silica membrane and the ultrafiltration membrane can be sufficiently observed and the thickness of the ultrafiltration membrane occupies at least about one-third of the field of view. For example, in the case where the thickness of the ultrafiltration membrane is 1 μm, the magnification is set to be about 50,000 times. Regarding the observed image, in the state in which the surface of the silica membrane 18 is placed upward and in a horizontal position, a horizontal line in contact with the uppermost portion of the ultrafiltration membrane 15 is drawn and, in addition, a horizontal line in contact with the lowermost portion of the ultrafiltration membrane 15 is drawn. The distance between, the horizontal lines is represented as the thickness (100%) of the ultrafiltration membrane 15. Subsequently, a region corresponding to 25% of the ultrafiltration membrane 15 from the silica membrane 18 is represented as the membrane-side region 16, and a region corresponding to 25% of the ultrafiltration membrane 15 from the support body 14 is represented as the base-material-side region 17. Then, 10 points are selected at random in the membrane-side region 16, EDX elementary analysis is performed, the number of atoms (at %) of Si and that of the element M (for example, Ti) are calculated, and the atomic ratio A (Si/M) is determined. Likewise, 10 points are selected at random in the base-material-size region 17, EDX elementary analysis is performed, and the atomic ratio B (Si/M) is determined. In this regard, EDX elementary analysis is performed at 10 points at random for the electron microscope observation of at least one field of view, and more preferably the electron microscope observation of a plurality of fields of view. For example, EDX elementary analysis may be performed at 2 points each of 5 fields of view. The 10 points of fields of view selected at random do not overlap one another. In addition, in order to avoid localized measurements, the range of a field of view of EDX analysis per measurement is set to be about 0.2 μm or more in the direction orthogonal to the membrane thickness and about X μm or more in the membrane thickness direction. In this regard, X μm is set to be the membrane thickness (μm) of the ultrafiltration membrane (membrane-side region or base-material-side region)×about 0.2 or more. The range of a field of view of EDX analysis is selected such that only the ultrafiltration membrane is included without including the silica membrane in the case of the membrane-side region 16 and without including tile base material in the case of the base-material-side region 17.

According to the silica membrane filter 10 of the present embodiment described above, the permeation rate during separation of the alcohol from the organic fluid mixture can be more increased. Here, in order to produce a dense silica membrane layer on the ultrafiltration membrane, it is considered that (1) the inside of the ultrafiltration membrane is filled with silica, (2) the silica sol is made to be hard-to-infiltrate into the ultrafiltration membrane by increasing the particle diameter and the viscosity of the silica sol, (3) the silica sol is made not to infiltrate Into the ultrafiltration membrane by increasing the resistance of the ultrafiltration membrane, and the like. In the case of (1), if the inside of the ultrafiltration membrane is filled with silica, the permeation resistance of the entire membrane produced increases, and the permeation rate of the fluid during separation of the fluid is reduced. In the case of (2), the reaction rate during formation of the silica sol is low depending on the raw material of the silica membrane, and it may be difficult to increase the particle diameter of the sol. In addition, if the viscosity is increased by increasing the silica sol concentration, the amount of silica sol that adheres at a time increases, and cracking of the membrane occurs. Meanwhile, if a solvent having a high viscosity is used, it is difficult to uniformly coating the ultrafiltration membrane during membrane formation, and a further problem occurs in that thickness variations occur in the membrane. In the case where the ultrafiltration membrane is not infiltrated by the raw material component of the silica membrane at all, as in the case of (3), cracking of the membrane may occur due to difference in the thermal expansion between the silica membrane and the surface of the ultrafiltration membrane during firing. Therefore, the inside of the ultrafiltration membrane has to be infiltrated by the silica membrane to the extent that the permeation resistance during liquid separation is minimized. Regarding the silica membrane filter according to the present embodiment, the atomic ratio A (Si/M) in the membrane-side region satisfies $0.01 \leq A \leq 0.5$, and the ratio A/B of the atomic ratio A to the atomic ratio B (Si/M) in the base-material-side region is within the range of 1.1 or more. Infiltration by the raw material component of the silica membrane can be controlled by, for example, increasing the resistance of the ultrafiltration membrane and, as a result, the permeation rate during separation from the organic fluid mixture can be further increased.

It is to be understood that the present invention is not limited to the embodiments described above and can be implemented in various aspects within the scope of the present invention.

EXAMPLES

Specific instances of production of a silica membrane filter will be described below as Examples.

Production, of Silica Membrane Filter

A porous alumina-based circular columnar member (monolithic shape member), which had 55 linear through holes (through holes) each having a diameter of 2.5 mm in the longitudinal direction and which had a diameter of 30 mm and a length of 160 mm, was produced by extrusion molding and firing. Subsequently, a microfiltration membrane of alumina and titania was made in each of the through holes, and firing was performed so as to produce a support body. Both end portions of the monolithic shape base material provided with the microfiltration membranes was sealed by using molten glass (seal portion). Then, an ultrafiltration membrane (UF membrane) of titania was formed in each of the through holes. Initially, a titania sol liquid was produced by hydrolyzing titanium propoxide in the presence of nitric acid. The sol particle diameter measured by a dynamic light scattering method was 100 nm. The resulting titania sol liquid was diluted with water, and PVA serving as an organic binder was appropriately added so as to produce a membrane-forming sol. Membranes were formed in base material cells by passing the membrane-forming sol through the cells to contact. Drying was performed and, thereafter, firing was performed at 375° C. to 500° C. The passing, drying, and firing steps were taken as one cycle of membrane formation, and 2 to 6 cycles were performed so as to produce a porous base material in which the ultrafiltration membrane was formed on the support body. After final firing was performed, the water permeate flow rate of the porous base material (support body and ultrafiltration membrane) was measured. The water permeate flow rate of the porous base material was adjusted by controlling the amount of the ultrafiltration membrane that adheres (membrane thickness) by the titania sol concentration and the number of times of membrane formation and controlling the pore diameter by the firing temperature and the amount of PVA added.

A silica membrane was produced by using p-tolyltrimethoxysilane or phenyltrimethoxysilane as silicon alkoxide having an aryl group. A mixed solution was produced by mixing p-tolyltrimethoxysilane and ethanol and performing agitation at 4° C. Subsequently, a nitric acid aqueous solution was added in small amounts so as to cause hydrolysis. After the nitric acid aqueous solution was added until the pH of the mixed solution reached 0.3, agitation was performed at 4° C. for 1 hour. Then, the resulting mixed solution was agitated at 50° C. for 3 hours so as to produce a reaction liquid. The pH was measured by a pH meter (Twin pH B-212, produced by HORIBA, Ltd.). Thereafter, the entire reaction liquid was diluted by adding ethanol such that the sol concentration of the reaction liquid became 2.0 percent by mass in terms of silica, and a precursor sol of silicon alkoxide having a p-tolyl group was produced.

After 160 mL of precursor sol was measured, the precursor sol was made to flow downward from one end surface of the above-described porous base material with both end surfaces sealed toy glass into the cells (through holes). As a result, the inner wall surfaces of the cells were coated with the precursor sol. Then, the precursor sol was dried to produce a dried membrane. Thereafter, a fired membrane was formed by maintaining the dried membrane at 400° C. for 1 hour. The above-described fired-membrane-forming operation from coating with the precursor sol to the heat treatment was repeated predetermined times, and a silica membrane filter provided with a silica membrane having a p-tolyl group was produced. Also, the same steps were performed by using phenyltrimethoxysilane, and a silica membrane filter having a phenyl group was produced.

membrane was assumed to be the water permeate flow rate (m/day). In addition, a p-tolylsilica membrane was formed on the ultrafiltration membrane, where the silica sol concentration, the firing temperature, and the number of times of membrane formation were as shown in Table 1. The ultrafiltration membranes and the silica membranes produced under the conditions shown in Table 1 were taken as Examples 1 to 10 and Comparative Examples 1 to 4. In this regard, in Comparative Example 2, firing was not performed when the ultrafiltration membrane was formed but firing was performed at the same time with the silica membrane after the silica membrane was formed once.

TABLE 1

| | Titania sol concentration Mass % | Firing temperature ° C. | Number of times of membrane formation | Water permeate flow rate[1] m/day | UF pore diameter nm | UF membrane thickness μm | Aryl group | Silica sol concentration Mass % | Firing temperature ° C. | Number of times of membrane formation | Silica membrane thickness nm |
|---|---|---|---|---|---|---|---|---|---|---|---|
| Example 1 | 0.4 | 425 | 4 | 2.1 | 4 | 1.0 | p-tolyl | 2.0(1st) 0.7(2nd) | 400 | 2 | 80 |
| Example 2 | 0.4 | 425 | 6 | 1.5 | 4 | 1.2 | p-tolyl | 2.0(1st) 0.7(2nd) | 400 | 2 | 70 |
| Example 3 | 0.6 | 400 | 4 | 1.0 | 3 | 1.8 | p-tolyl | 2.0(1st) 0.7(2nd) | 400 | 2 | 120 |
| Example 4 | 0.6 | 400 | 6 | 0.9 | 3 | 2.5 | p-tolyl | 1.0(1st) 0.7(2nd) | 400 | 2 | 170 |
| Example 5 | 0.4 | 500 | 4 | 4.2 | 8 | 0.8 | p-tolyl | 2 | 400 | 2 | 100 |
| Example 6 | 0.4 | 425 | 2 | 5.0 | 4 | 0.4 | p-tolyl | 2.0(1st) 0.7(2nd) | 400 | 2 | 30 |
| Example 7 | 0.4 | 425 | 4 | 2.1 | 4 | 1.0 | phenyl | 2.0(1st) 0.7 (2nd 3rd) | 400 | 3 | 50 |
| Example 8 | 0.6 | 375 | 4 | 1.0 | 2 | 1.7 | phenyl | 2 | 375 | 2 | 150 |
| Example 9 | 0.8 | 450 | 2 | 3.4 | 6 | 0.9 | phenyl | 2 | 425 | 2 | 30 |
| Example 10 | 0.4 | 425 | 4 | 2.1 | 4 | 1.0 | p-tolyl | 2.0(1st) 0.7(2nd) | 375 | 2 | 100 |
| Comparative Example 1 | 0.4 | 500 | 2 | 6.5 | 8 | 0.2 | p-tolyl | 2 | 400 | 2 | 100 |
| Comparative Example 2 | 1.6 | — | 1 | — | — | — | p-tolyl | 2 | 400 | 1 | 200 |
| Comparative Example 3 | 0.4 | 500 | 2 | 6.5 | 8 | 0.2 | p-tolyl | 1.0(1st) 0.7(2nd) | 400 | 2 | <10 |
| Comparative Example 4 | 0.4 | 425 | 4 | 2.1 | 4 | 1.0 | phenyl | 1.0(1st) 0.7(2nd) | 400 | 2 | <10 |

[1]The water permeate flow rate of the monolithic shape base material and the ultrafiltration membrane (UF membrane)

Examples 1 to 10 and Comparative Examples 1 to 4

Each of ultrafiltration membranes was produced where the titania sol concentration, the firing temperature, and the number of times of membrane formation were as shown in Table 1. The water permeate flow rate of the resulting ultrafiltration membrane was also shown in Table 1. The water permeate flow rate was as described below. Initially, a seal portion was disposed on the outlet side of the silica membrane filter so as to create a state in which one end of each of the cells was sealed. Distilled water was supplied to the cells from the inlet side, and the flow rate, the pressure, and the water temperature of the supplied water were measured. The resulting values were converted to values under the condition of pressurization of 0.1 MPa at 25° C., and the amount of water ($m^3$) that passed a unit area of the Pore Diameter of Ultrafiltration Membrane The average pore diameter of the ultrafiltration membrane was determined from pore diameter distribution obtained by passing hexane and nitrogen at the same time through the ultrafiltration membrane, changing the partial pressure of hexane and measuring the nitrogen permeate flow rate at that time, and substituting the measurement value of the hexane partial pressure into the Kelvin equation of condensation (refer to Journal of Membrane Science 186 (2001) 257-265). The nitrogen permeate flow rate at the hexane partial pressure of 0 was assumed to be 1, and the pore diameter when the value thereof became half was assumed to be the average pore diameter.

Amount of Silica Membrane Infiltrated

Figure 4:
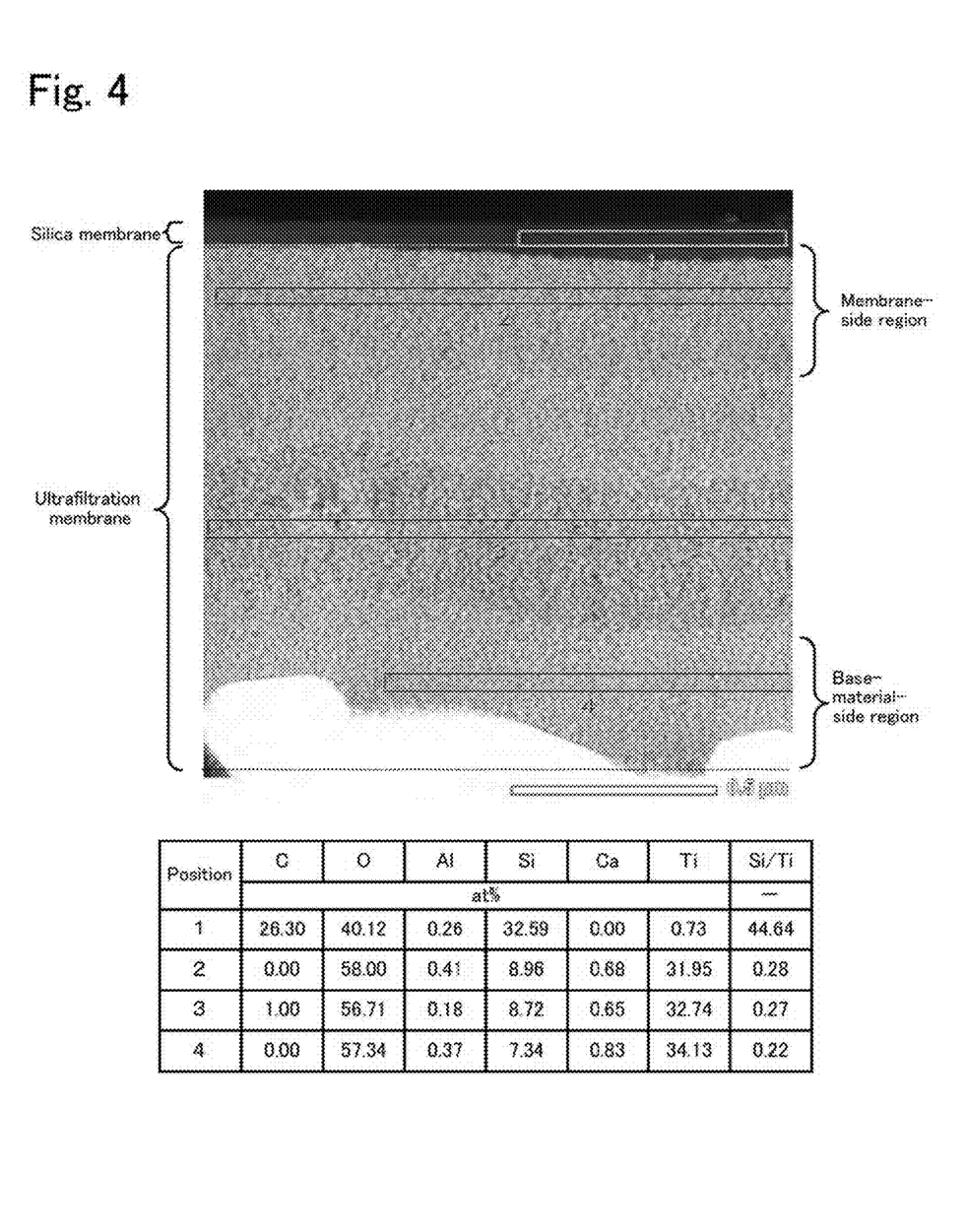
FIG. 4 shows an electron micrograph and EDX measurement results of the silica membrane filter according to Example 1.

A cross section of the resulting silica membrane filter was subjected to EDX elementary analysis of the ultrafiltration membrane. EDX elementary analysis was performed with respect to 10 points selected at random in a region (membrane-side region) corresponding to 25% of the ultrafiltration membrane on the silica membrane side (upper portion) and composed of the ultrafiltration membrane. The average value thereof was assumed to be the atomic ratio A (=Si/Ti) of Si to Ti in the membrane-side region. Meanwhile, EDX elementary analysis was performed with respect to 10 points selected at random in a region (base-material-side region) corresponding to 25% of the ultrafiltration membrane on the base material side (lower portion) and composed of the ultrafiltration membrane. The average value thereof was assumed to be the atomic ratio B (=Si/Ti) of Si to Ti in the base-material-side region. Then, the ratio A/B of the atomic ratio A to the atomic ratio B was determined. The range of a field of view of EDX analysis per measurement was set to be about 0.2 μm or more in the direction orthogonal to the membrane thickness and about X μm or more in the membrane thickness direction. This X μm was set to be the membrane thickness (μm) of the ultrafiltration membrane (membrane-side region or base-material-side region)×about 0.25 or more. FIG. 4 shows an electron micrograph and EDX measurement results of the silica membrane filter according to Example 1.

Pervaporation Test 1

A liquid mixture of ethanol and isooctane was prepared to satisfy ethanol:isooctane=10:90 on a mass ratio basis. The above-described liquid mixture at a temperature of 60° C. was made to pass through the cells of the silica membrane filter, decompression was performed from the side surface of the silica membrane filter at a degree of vacuum of 6 kPa, and a permeated vapor that went out through the side surface of the silica membrane filter was collected with a trap cooled by liquid nitrogen. The total permeate flux was calculated from the mass of a liquefied material of the permeated vapor collected. Also, the liquefied material of the permeated vapor was analyzed by gas chromatography, and the composition of the permeated vapor was determined.

Pervaporation Test 2

A liquid mixture of ethanol, n-octane, and o-xylene was prepared to satisfy ethanol:n-ooctane:o-xylene=10:45:45 on a mass ratio basis. The above-described liquid mixture at a temperature of 70° C. was made to pass through the cells of the silica membrane filter, decompression was performed from the side surface of the silica membrane filter at a degree of vacuum of 6 kPa, and a permeated vapor that went out through the side surface of the silica membrane filter was collected with a trap cooled by liquid nitrogen. The total permeate flux was calculated from the mass of a liquefied material of the permeated vapor collected. Also, the liquefied material of the permeated vapor was analyzed by gas chromatography, and the composition of the permeated vapor was determined.

Result and Consideration

Tables 2 and 3 show the degree of infiltration into the ultrafiltration membrane of the silica membrane filter and the results of the pervaporation tests of Examples 1 to 10 and Comparative Examples 1 to 4. As shown in Tables 1 to 3, regarding the Examples, the atomic ratio A that was Si/Ti on the silica membrane side (membrane-side region) in the ultrafiltration membrane was within the range of 0.1 to 0.5, and the ratio (A/B) of the atomic ratio A to the atomic ratio B that was Si/Ti on the base material side (base-material-side region) was within the range of 1.1 to 5.2. That is, in the ultrafiltration membrane of each of Examples 1 to 7, there was a concentration, gradient of Si from the silica membrane side to the base material side. Further, in the Examples, as the water permeate flow rate of the base material and the ultrafiltration membrane decreased, the permeation rate during separation of the ethanol/isooctane liquid mixture increased. Therefore, it was conjectured that the separation performance of the liquid mixture was improved because infiltration of silica into the ultrafiltration membrane was reduced. On the other hand, regarding Comparative Example 1 in which the water permeate flow rate was large, infiltration of silica into the ultrafiltration membrane increased and the permeation rate was low. Further, regarding Comparative Example 2 in which firing in formation of the ultrafiltration membrane was not performed and co-firing with the silica membrane was performed, the silica membrane did not infiltrate into the ultrafiltration membrane at all, and the liquid mixture could not be separated. It was conjectured that this was an influence of occurrence of cracking of the membrane during firing.

In addition, according to pervaporation test 2, it was found that o-xylene preferentially permeated next to ethanol, as shown in Table 3. In general, it is considered that n-octane is a straight-chain hydrocarbon and is a component having a molecular diameter smaller than o-xylene, which is an aromatic compound, and n-octane easily permeates the membrane. However, regarding the present membrane, there was a tendency of o-xylene having a large molecular diameter to easily permeate. The reason for this is conjectured as described below. For example, it was considered that the pore of the silica membrane formed by an aryl group being burnt off had a planar pore shape similar to the aryl group, and the pore shape was a shape suitable for permeation of o-xylene which was an aromatic component also having a planar molecular shape. As a result, it was conjectured that o-xylene preferentially permeated the silica membrane filter of the present Example compared with n-octane which did not have a planar structure.

When Example 5 was compared with Comparative Example 1, the state of the UF membrane was different due to a difference in the number of times of membrane formation, the A/B ratio was large, and the ethanol permeation performance and the n-octane/o-xylene selectivity were higher. Regarding Comparative Example 1, it was conjectured that the UF membrane was in the state of being infiltrated by a higher proportion of silica and the ethanol permeation rate and the concentration were low. When Comparative Example 3 was compared with Comparative Example 1, the state of the UF membrane was the same but the silica membrane was thin and, therefore, the permeated ethanol concentration was low, the n-octane/o-xylene selectivity was poor, and the separation accuracy was low. When Example 7 was compared with Comparative Example 4, the state of the UF membrane was the same but the membrane formation conditions for the silica membrane were different and, therefore, the A/B was larger and the silica membrane was sufficiently formed. Consequently, regarding Example 7, the ethanol permeation performance was high and the n-octane/o-xylene selectivity and the like were high.

As described above, it was found that, in the case where the water permeate flow rate (pore diameter and membrane thickness) of the ultrafiltration membrane was made to be appropriate and infiltration by the silica sol was made optimum in the structure, the permeation resistance was small and the permeation rate during separation of alcohol from the organic fluid mixture could be increased.

TABLE 2

|  | Upper portion of UF membrane (membrane-side region) Si/Ti (A) | Lower portion of UF membrane (base-material-side region) Si/Ti (B) | Si/Ti ratio (A/B) | Ethanol permeation rate kg/m²/hr | Permeated ethanol concentration Mass % |
|---|---|---|---|---|---|
| Example 1 | 0.28 | 0.23 | 1.3 | 4.0 | 92 |
| Example 2 | 0.25 | 0.15 | 1.7 | 4.5 | 88 |
| Example 3 | 0.13 | 0.07 | 1.9 | 3.7 | 98 |
| Example 4 | 0.09 | 0.03 | 3.0 | 3.2 | 99 |
| Example 5 | 0.46 | 0.38 | 1.2 | 3.5 | 95 |
| Example 6 | 0.44 | 0.40 | 1.1 | 2.9 | 80 |
| Example 7 | 0.41 | 0.26 | 1.6 | 3.8 | 82 |
| Example 8 | 0.30 | 0.058 | 5.2 | 2.4 | 85 |
| Example 9 | 0.48 | 0.41 | 1.2 | 4.2 | 78 |
| Example 10 | 0.25 | 0.20 | 1.3 | 2.4 | 98 |
| Comparative Example 1 | 0.53 | 0.54 | 1.0 | 2.0 | 70 |
| Comparative Example 2 | Below the measurable limit | | — | Undiluted solution is permeated | |
| Comparative Example 3 | 0.30 | 0.31 | 1.0 | 4.0 | 38 |
| Comparative Example 4 | 0.25 | 0.26 | 1.0 | 4.9 | 42 |

TABLE 3

|  | Ethanol permeation rate kg/m²/hr | Permeation rate of n-octane kg/m²/hr | Permeation rate of o-xylene kg/m²/hr | Permeated ethanol concentration Mass % | o-xylene/n-octane ratio |
|---|---|---|---|---|---|
| Example 1 | 9.6 | 0.6 | 1.9 | 79 | 3.2 |
| Example 2 | 10.5 | 1.0 | 1.7 | 80 | 1.7 |
| Example 3 | 8.7 | 0.3 | 1.8 | 81 | 6.0 |
| Example 4 | 6.5 | 0.1 | 0.4 | 93 | 4.0 |
| Example 5 | 7.9 | 0.5 | 1.7 | 78 | 3.4 |
| Example 6 | 5.6 | 1.0 | 1.8 | 67 | 1.8 |
| Example 7 | 6.1 | 0.5 | 2.4 | 68 | 4.8 |
| Example 8 | 5.3 | 0.8 | 2.1 | 65 | 2.6 |
| Example 9 | 7.3 | 1.5 | 2.6 | 64 | 1.7 |
| Example 10 | 5.1 | 0.4 | 0.7 | 82 | 1.8 |
| Comparative Example 1 | 3.7 | 1.3 | 1.5 | 57 | 1.2 |
| Comparative Example 2 | Undiluted soluton is permeated | | | | |
| Comparative Example 3 | 9.2 | 6.1 | 4.8 | 45.8 | 0.8 |
| Comparative Example 4 | 9.3 | 4.5 | 4.6 | 50.4 | 1.0 |

It is to be understood that the present invention is not limited to the Examples described above and can be implemented in various aspects within the scope of the present invention.

The present application claims priority from Japanese Patent Application No. 2015-055918 filed on Mar. 19, 2015, the entire contents of which are incorporated herein by reference.

What is claimed is:

1. A silica membrane filter comprising:
an ultrafiltration membrane which is disposed on a support body and which contains an element M as a primary component; and
a silica membrane which is disposed on the ultrafiltration membrane and which was produced using an aryl group,
wherein the ultrafiltration membrane has a structure infiltrated by Si of the silica membrane, the atomic ratio A (=Si/M) of Si to the element M in a membrane-side region, which is a region corresponding to 25% of the ultrafiltration membrane from the silica membrane, satisfies 0.01≤A≤0.5, and the ratio A/B of the atomic ratio A to the atomic ratio B (=Si/M) in a base-material-side region, which is a region corresponding to 25% of the ultrafiltration membrane from the support body, is within the range of 1.1 or more.

2. The silica membrane filter according to claim 1, wherein the silica membrane was produced using at least one of a p-tolyl group and a phenyl group.

3. The silica membrane filter according to claim 1, wherein the atomic ratio A of the ultrafiltration membrane satisfies 0.1≤A≤0.5.

4. The silica membrane filter according to claim 1, wherein the ratio A/B of the ultrafiltration membrane satisfies 1.2≤A/B.

5. The silica membrane filter according to claim 1, wherein the atomic ratio B of the ultrafiltration membrane satisfies 0.01≤B≤0.4.

6. The silica membrane filter according to claim 1, wherein the average pore diameter of the ultrafiltration membrane is within the range of 2 nm or more and 20 nm or less.

7. The silica membrane filter according to claim 1, wherein the membrane thickness of the ultrafiltration membrane is within the range of 0.3 µm or more and 5 µm or less.

8. The silica membrane filter according to claim 1, wherein the element M that is a primary component of the ultrafiltration membrane is Ti.

9. The silica membrane filter according to claim 1, wherein the membrane thickness of the silica membrane is within the range of 30 nm or more and 200 nm or less.

* * * * *